United States Patent [19]

Burdette et al.

[11] Patent Number: 5,391,197
[45] Date of Patent: Feb. 21, 1995

[54] ULTRASOUND THERMOTHERAPY PROBE

[75] Inventors: Everette C. Burdette, Champaign, Ill.; Richard diMonda, Marietta, Ga.

[73] Assignee: Dornier Medical Systems, Inc., Champaign, Ill.

[21] Appl. No.: 83,967

[22] Filed: Jun. 25, 1993

Related U.S. Application Data

[63] Continuation-in-part of Ser. No. 976,232, Nov. 13, 1992.

[51] Int. Cl.⁶ ............................................. A61F 7/12
[52] U.S. Cl. ................................. 607/97; 607/154
[58] Field of Search ............... 128/662.03; 607/96–97, 607/104, 154–156

[56] References Cited

U.S. PATENT DOCUMENTS 4,977,902 12/1990 Sekino et al. ..................... 607/97

FOREIGN PATENT DOCUMENTS 0370890 5/1990 European Pat. Off. .

OTHER PUBLICATIONS

"Prostatic and Periprostatic Interstitial Temp. Measurements in Patients Treated with Transrectal Thermal Therapy (Local Intracavitary Microwave Hyperthermia)"; Kaplan et al.; The Journal of Urology, vol. 147, pp. 1562–1564; Jun. 1992.
"Introduction to Hyperthermia Device Evaluation"; M. D. Sapozink et al.; Int. J. Hypethermia; vol. 4(1); pp. 1–15—1988.
"Clin. Evaluation of Hyperthermia Equipment: The Univ. of Arizona Institutional Report for the NCI Hyperthermia Evaluation Contract"; Shimm et al; Int. J. Hyperthermia, vol. 4(1), pp. 39–51 (1988).
"Stanford Univ. Institutional Report–Phase 1 Eval. of Equipment for Hyperthermia Treatment of Cancer"; Kapp et al.; Int. J. Hyperthermia; vol. 4(1); pp. 75–115; (1988).
"High Freq. Transmitter for the Localized Heat Treatment of the Prostate Gland"; Petrowicz et al.; National Cancer Institute Monograph No. 61 pp. 473–476 (1982).
"Induction of Hyperthermia in Deep Seated Tumors by a Special Microwave Applicator"; Mendecki et al.; Proc. of the 2nd International Symposium; Essen; Jun. 2–4 1977.

*Primary Examiner*—Angela D. Sykes
*Attorney, Agent, or Firm*—Reinhart, Boerner, Van Deuren, Norris & Rieselbach

[57] ABSTRACT

A thermotherapy method for treatment of prostate tissues. The thermotherapy method comprises the steps of locating a cylindrical ultrasound transducer substantially within an applicator housing, dimensioning the cylindrical ultrasound transducer to have a radius of curvature larger than a radius of curvature of the applicator housing, and providing a power source for the ultrasound transducer to produce a focused energy field.

19 Claims, 14 Drawing Sheets

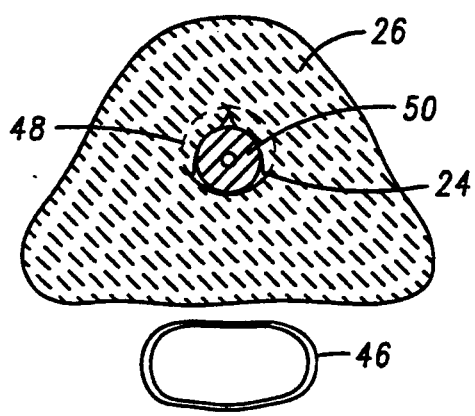
Fig. 6
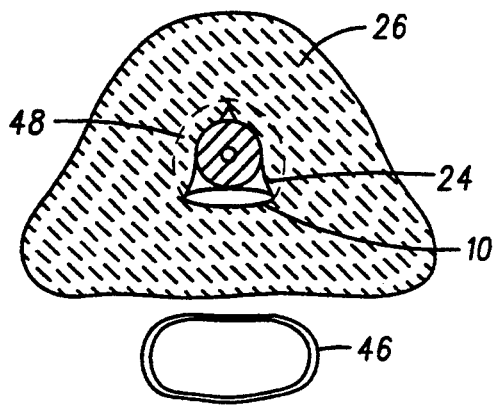
Fig. 7
Fig. 8
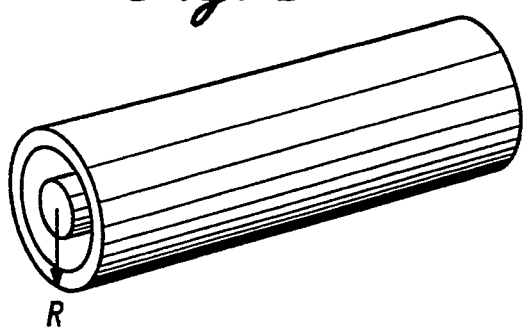
Fig. 9
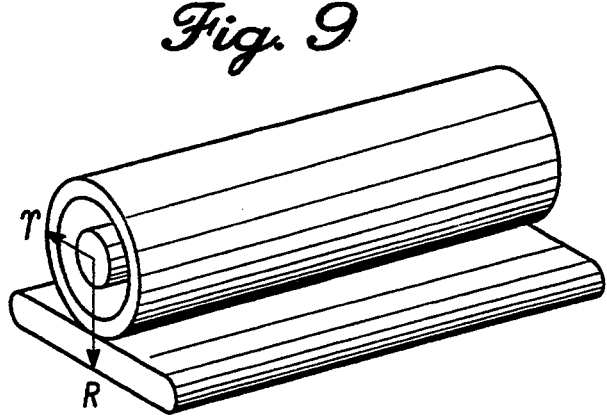
Fig. 10
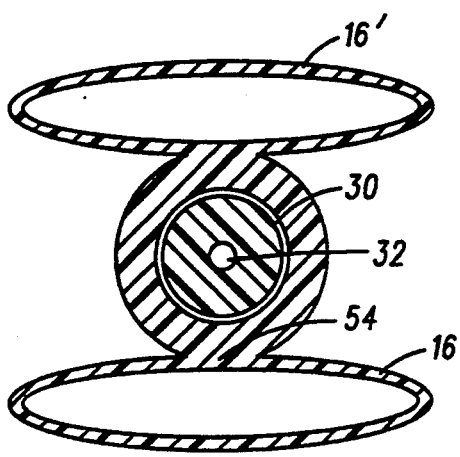

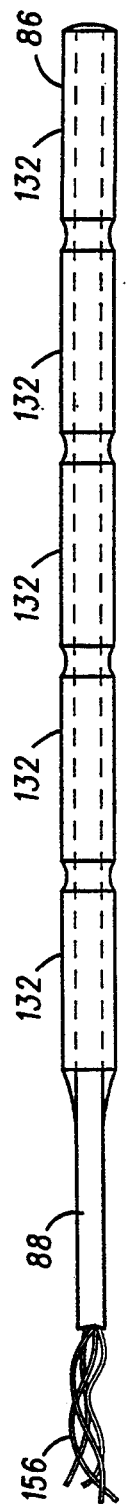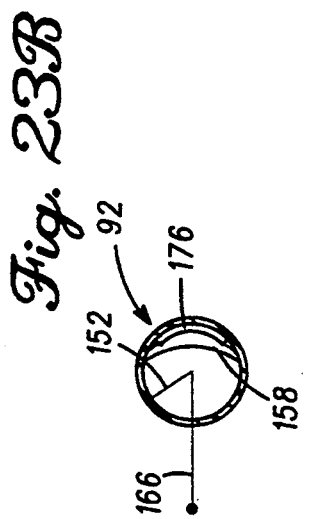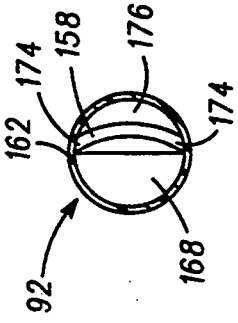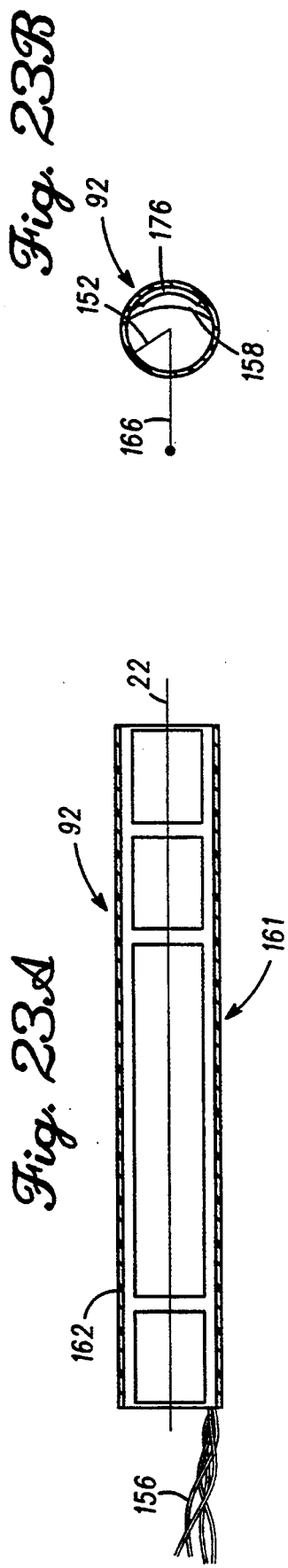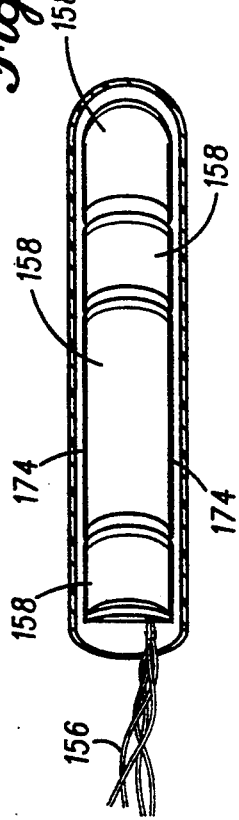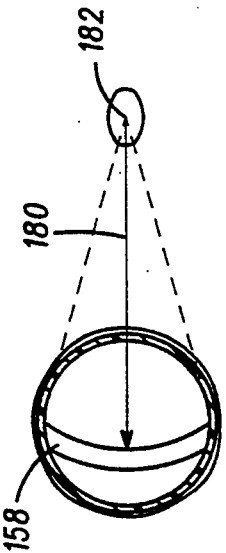

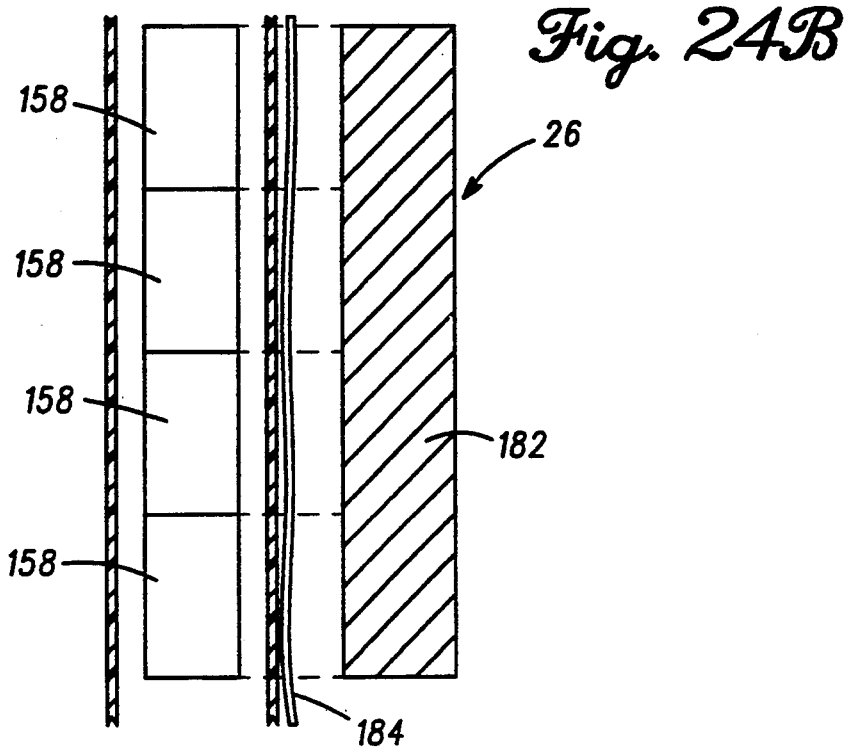
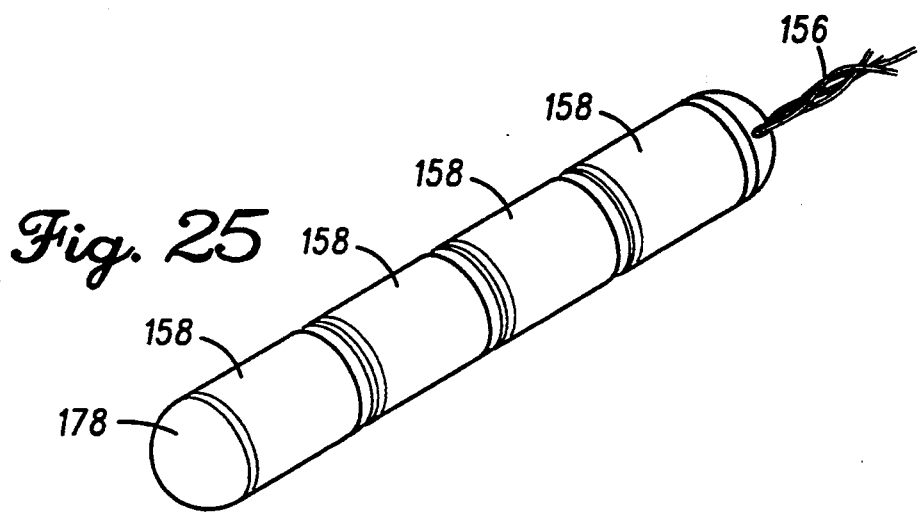
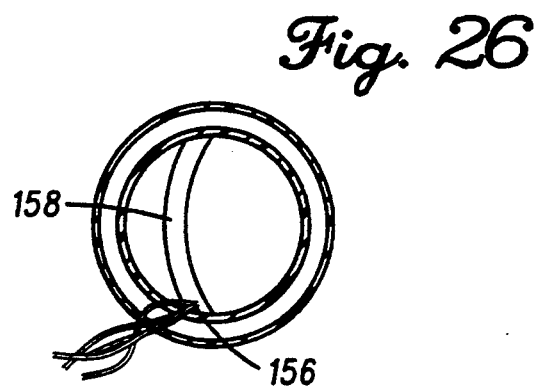

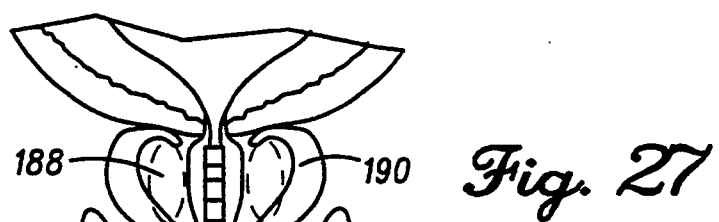
Fig. 27
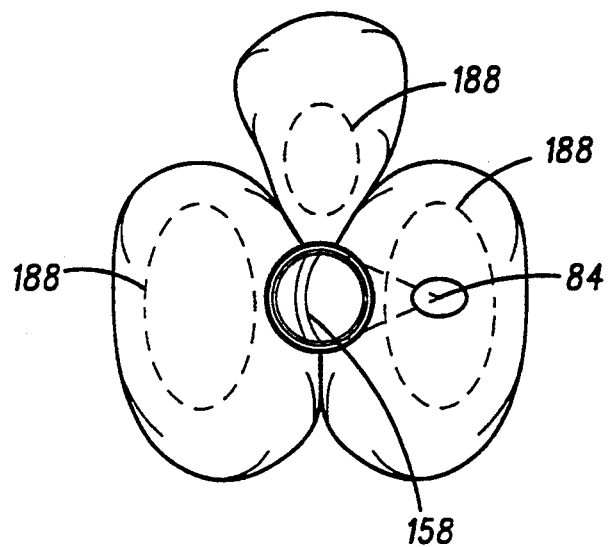
Fig. 28
Fig. 29
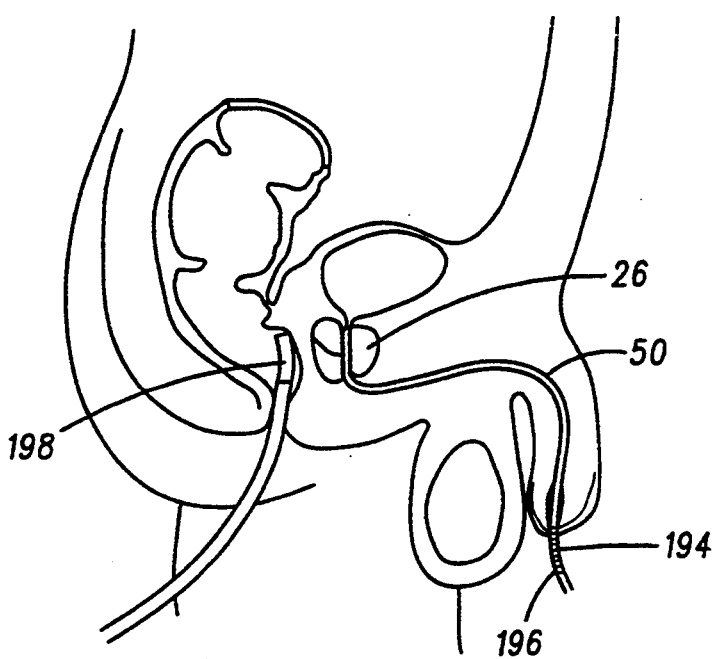

ULTRASOUND THERMOTHERAPY PROBE

This application is a continuation-in-part of U.S. Ser. No. 07/976,232, filed Nov. 13, 1992.

The present invention relates generally to an apparatus and method for performing a thermotherapy patient treatment protocol. More particularly, the invention relates to a novel apparatus and method for irradiating and/or heating internal organs, such as the prostate gland, for therapeutic purposes.

Thermotherapy treatment is a relatively new method of treating diseased and/or undesirably enlarged human tissues. Hyperthermia treatment is well known in the art, involving the maintaining of a temperature between about 41.5° through 45° C. Thermotherapy, on the other hand, usually requires energy application to achieve a temperature above 45° C. for the purposes of coagulating the target tissue. Tissue coagulation beneficially changes the density of the tissue. As the tissue shrinks, forms scars and is reabsorbed, the impingement of the enlarged tissues, such as an abnormal prostate, is substantially lessened.

The higher temperatures required by thermotherapy require delivery of larger amounts of energy to the target tissues. At the same time, it is important to shield nontarget tissues from the high thermotherapy temperatures used in the treatment. Providing safe and effective thermotherapy, therefore, requires devices which have further capabilities compared to those which are suitable for hyperthermia.

Though devices and methods for treating benign prostatic hyperplasia have evolved dramatically in recent years, significant improvements have not occurred and such progress is badly needed. As recently as 1983, medical textbooks recommended surgery for removing impinging prostatic tissues and four different surgical techniques were utilized. Suprapubic prostatectomy was a recommended method of removing the prostate tissue through an abdominal wound. Significant blood loss and the concomitant hazards of any major surgical procedure were possible with this approach.

Perineal prostatectomy was an alternatively recommended surgical procedure which involved gland removal through an incision in the perineum. Infection, incontinence, impotence or rectal injury were more likely with this method than with alternative surgical procedures.

Transurethral resection of the prostate gland has been another recommended method of treating benign prostatic hyperplasia. This method required inserting a rigid tube into the urethra. A loop of wire connected with electrical current was rotated in the tube to remove shavings of the prostate at the bladder orifice. In this way, no incision was needed. However, strictures were more frequent and repeat operations were sometimes necessary.

The other recommended surgical technique for treatment of benign prostatic hyperplasia was retropubic prostatectomy. This required a lower abdominal incision through which the prostate gland was removed. Blood loss was more easily controlled with this method, but inflammation of the pubic bone was more likely.

With the above surgical techniques, the medical textbooks noted the vascularity of the hyperplastic prostate gland and the corresponding dangers of substantial blood loss and shock. Careful medical attention was necessary following these medical procedures.

The problems previously described led medical researchers to develop alternative methods for treating benign prostatic hyperplasia. Researchers began to incorporate heat sources in Foley catheters after discovering that enlarged mammalian tissues responded favorably to increased temperatures. Examples of devices directed to treatment of prostate tissue include U.S. Pat. No. 4,662,383 (Harada), U.S. Pat. No. 4,967,765 (Turner), U.S. Pat. No. 4,662,383 (Sogawa) and German Patent No. DE 2407559 C3 (Dreyer). Though these references disclosed structures which embody improvements over the surgical techniques, significant problems still remain unsolved.

Recent research has indicated that enlarged prostate glands are most effectively treated with higher temperatures than previously thought. Complete utilization of this discovery has been tempered by difficulties in shielding rectal wall tissues and other nontarget tissues. While shielding has been addressed in some hyperthermia prior art devices, the higher energy field intensities associated with thermotherapy necessitate structures having further capabilities beyond those suitable for hyperthermia. For example, the symmetrical devices disclosed in the above-referenced patents have generally produced relatively uniform cylindrical energy fields. Even at the lower energy field intensities encountered in hyperthermia treatment, unacceptably high rectal wall temperatures have limited treatment periods and effectiveness. Further, while shielding using radioreflective fluid has been disclosed in the prior art (see for example European Patent Application No. 89,403,199) the location of such radioreflective fluid appears to increase energy field intensity at the bladder and rectal wall. This is contrary to one of the objects of the present invention.

Additionally, many prior art references appear to require traditional rubber anchoring balloons for secure placement and retention of a variety of treatment and bladder drainage devices. Further, these devices are typically flexible and have no stiffening capability for straightening the treatment path for more efficient and consistent treatment.

In addition, efficient and selective cooling of the devices is rarely provided. This increases patient discomfort and increases the likelihood of healthy tissue damage. These problems have necessitated complex and expensive temperature monitoring systems along the urethral wall.

Finally, the symmetrical designs of the above-referenced devices do not allow matching of the energy field to the shape of the abnormally enlarged prostate gland. Ideally, the energy field reaching the tissues should be asymmetric and generally should expose the upper and lateral (side) impinging lobes of the prostate gland to the highest energy. In addition, the field is ideally substantially elliptical such that the energy reaching the sphincters is minimized.

It is therefore an object of the invention to provide an improved apparatus and method suitable for ultrasound treatment of tissue.

It is a further object of the invention to provide an improved apparatus and method for thermotherapy treatment which provides a focused ultrasound energy pattern on target tissues.

It is yet a further object of the invention to provide a novel method and apparatus having a cylindrical ultrasound transducer with a radius of curvature larger than the housing for the transducer.

It is yet another object of the invention to provide an improved applicator designed to be inserted into an orifice of a male patient, wherein the applicator includes an arcuate whose longitudinal axis is parallel to the axis of the housing of the applicator.

It is a further object of the invention is to provide an improved arcuate ultrasound transducer providing a line focus of ultrasound energy on tissue to be treated.

It is a still further object of the invention to provide a novel means for dynamic monitoring of the treatment temperature distribution and to use such information to aid in the control of the deposited power level and its distribution.

It is another object of the invention to provide an improved ultrasonic applicator which can be inserted into the urethra and can be positioned with respect to the prostate and maintained in position during treatment.

It is yet another object of the invention to provide a novel means for diagnostic imaging of the prostate during treatment and monitoring the position of the applicator during treatment.

It is a still further object of the invention to provide an improved probe containing an array of ultrasound transducers for medical therapy purposes, and more particularly to a combined ultrasound transducer applicator and catheter for effective heating/insonation of the prostate of a male patient with acoustic energy for treating benign prostatic hypertrophy or prostatic cancer.

It is yet another object of the invention to provide a novel apparatus and method using a transducer array for the measurement of temperature changes with the treated tissues.

It is a further object of the invention to provide an improved method and apparatus using ultrasound energy for the treatment of prostate disease and, more particularly to provide an ultrasound applicator consisting of multiple transducers which can be inserted into the urethra or rectum and direct the energy in such a manner as to selectively treat the prostate gland.

It is yet another object of the invention to provide a novel method and apparatus utilizing ultrasound energy to achieve therapeutic temperatures in the prostate with better control of power deposition spatially within the prostate gland than is possible with prior art devices.

It is an additional object of the invention to provide an array of ultrasound transducers producing an energy field having a gap or "dead zone" whereby tissues located in this region are protected from energy transmission.

It is a further object of the invention to provide improved control of both the ultrasonic power level and the distribution of the power deposited in the prostate in a dynamic fashion which compensates for physiological changes (temperature, blood flow effects) that can occur during therapy and accommodates operator-desired alterations in the therapeutic energy distribution within the prostate.

It is a still further object of the invention to provide an improved thermal therapy applicator providing a focused application of energy.

It is yet another object of the invention to provide a novel method and apparatus for producing a line focus of ultrasound energy.

It is another object of the invention to provide an improved thermotherapy device which includes a collimated irradiation of a target zone generally and selective cooling of nontarget tissues.

It is an additional object of the invention to provide a plurality of ultrasound transducers having differing radii of curvature which can be selected to provide optimally-shaped energy fields for selected tissues, including, but not limited to, the lobes of a human prostate gland.

It is yet another object of the invention to provide an improved thermotherapy device which is capable of carrying a sound absorptive or reflective substance in one or more chambers, while utilizing a sound transparent substance in at least one other passage.

It is yet a further object of the invention to provide an improved thermotherapy device which is capable of carrying radioreflective and/or radiation absorptive fluid in one or more cooling chambers, while utilizing radiotransparent liquid in one or more cooling passages.

It is still another object of the invention to provide an improved thermotherapy device which is capable of carrying a light absorptive or reflective substance in one or more chambers, while utilizing a light transparent substance in at least one other passage.

It is yet an additional object of the invention to provide a novel thermotherapy device having at least one chamber capable of being lined with a substance which is reflective or absorptive to light, sound or microwaves.

It is still an additional object of the invention to provide a novel thermotherapy device having two or more chambers wherein a chamber located adjacent to the target tissue can be maintained at higher temperatures than the one or more chambers adjacent nontarget tissues.

It is a still further object of the invention to provide an improved method and apparatus for thermotherapy treatment which substantially straightens the tissue treatment region for more consistent and effective treatment of the desired tissue.

It is still an additional object of the invention to provide an improved thermotherapy device which reduces tissue damage and discomfort by providing more effective cooling to nontarget tissues.

It is yet another object of the invention to provide a novel thermotherapy apparatus which can be retained in a selectable treatment position with one or more extended, expandable balloons.

It is still a further object of the invention to provide a novel thermotherapy apparatus which can be retained in a selectable treatment position with one or more selectively extendable and expandable balloons.

It is an additional object of the invention to provide an improved thermotherapy apparatus having one or more extended, and nondistensible but expandable balloons in combination with a conventional anchor balloon for increased anchoring forces.

It is yet a further object of the invention to provide a novel thermotherapy apparatus which includes energy means (including, but not limited to, ultrasound, microwave or laser means) in combination with one or more extended, expandable balloons.

It is still a further object of the invention to provide an improved thermotherapy device which substantially conforms to, and therefore can more effectively treat, an asymmetrically enlarged mammalian organ.

It is an additional object of the invention to provide an improved thermotherapy device which includes ultrasound transducers, an antenna, or other energy sources capable of producing a substantially asymmetric energy output field, thus minimizing energy reaching the rectal wall in benign prostatic hyperplasia thermotherapy treatment.

It is still a further object of the invention to provide an improved thermotherapy apparatus which produces an energy field shaped in accordance with the enlarged mammalian gland to be treated.

It is still an additional object of the invention to provide a remote temperature sensing method using input and output cooling fluid temperatures to predict tissue temperatures.

It is yet a further object of the invention to provide an improved transrectal temperature and position sensing device.

Other advantages and features of the invention, together with the organization and manner of operation thereof, will become apparent from the following detailed description when taken in conjunction with the accompanying drawings, wherein like elements have like numerals throughout the drawings.

BRIEF DESCRIPTION OF THE DRAWINGS

FIG. 6 shows a cross-sectional view of a diseased prostate gland with a traditional treatment device inserted therein:

FIG. 7 illustrates a cross-sectional view of a diseased prostate gland with a thermotherapy device constructed in accordance with one form of the invention inserted therein;

FIG. 8 shows an isometric view of a symmetrical thermotherapy device;

FIG. 9 illustrates an isometric view of an asymmetrical thermotherapy device constructed in accordance with the invention;

FIG. 10 shows an alternative embodiment of a thermotherapy device including two secondary cooling lumens;

FIG. 22 illustrates an array of cylindrical transducer sections which can produce a segmented longitudinal line focus which can be radially rotated within a delivery system catheter;

FIG. 23A illustrates a side view of a preferred embodiment of an ultrasound probe; FIG. 23B shows an end view of the cylindrical line focus embodiment illustrated in FIG. 23A; FIG. 23C illustrates a crosssectional end view of a suitable water flow configuration for the device shown in FIGS. 23A and 23B; and FIG. 23D shows a perspective view of the ultrasound thermotherapy probe shown in FIGS. 23A, 23B, and 23C;

FIG. 24A shows a cross-sectional view of a line focus focal zone and FIG. 24B shows a longitudinal top view of the line focus focal zone obtainable with an ultrasound thermotherapy probe constructed in accordance with one form of the invention;

FIG. 25 illustrates convex transducers arranged in a flexible plastic tube or sheath;

FIG. 26 shows a cross-sectional view of a transducer mounting;

FIG. 27 shows a longitudinal cross-sectional view of zones of prostatic tissue destruction;

FIG. 28 illustrates lateral and median lobe zones of prostatic tissue destruction;

FIG. 29 shows a graduated ultrasound thermotherapy probe inserted in a human body in conjunction with a graduated transrectal probe used for ultrasonic imaging of the ultrasound applicator;

DETAILED DESCRIPTION OF THE PREFERRED EMBODIMENT

Figure 1A:
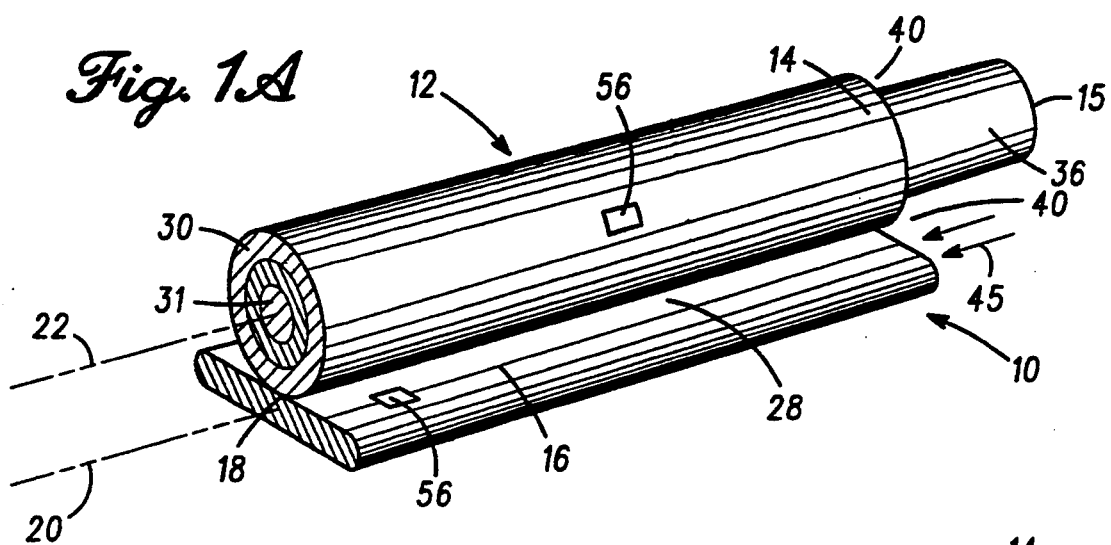
FIG. 1A illustrates an isometric view of a thermotherapy device constructed in accordance with one form of the invention.

Referring now to the figures and more particularly to FIG. 1A, a thermotherapy device constructed in accordance with the invention is indicated generally at 10. Throughout the application when referring to "thermotherapy," this terminology shall be meant to include both thermotherapy treatment as well as hyperthermia treatment unless specifically stated to exclude one therapy. An applicator portion 12 of the thermotherapy device 10 includes a primary cooling lumen 14 and a secondary cooling lumen 16. In the preferred form of this invention, "lumen" shall be used to refer to an inflatable and substantially nondistensible structure. The primary cooling lumen 14 and the secondary cooling lumen 16 are disposed adjacent to one another (and can be connected) at perimeter 18 so that their longitudinal axes 22 and 20, respectively, are substantially parallel.

Figure 2:
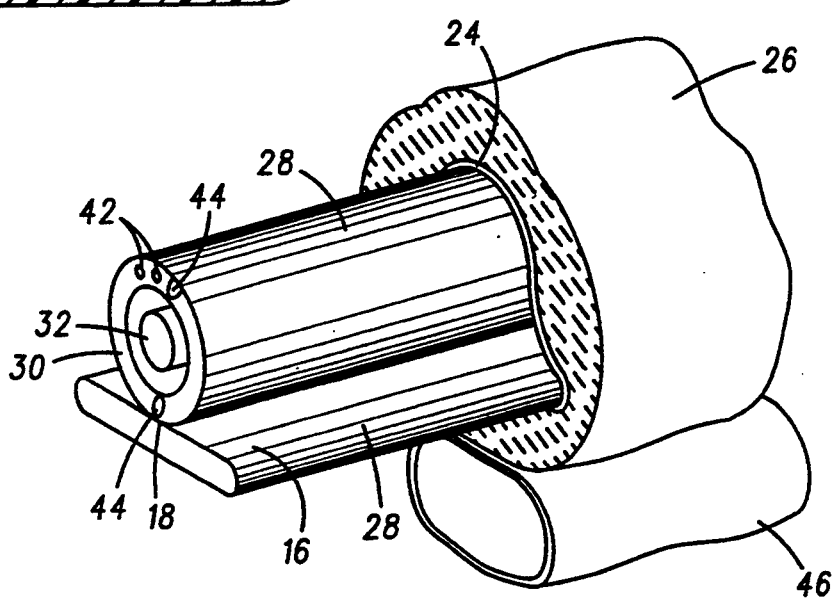
FIG. 2 shows an isometric view of a thermotherapy device as it is inserted into the prostate via the urethra.
Figure 3A:
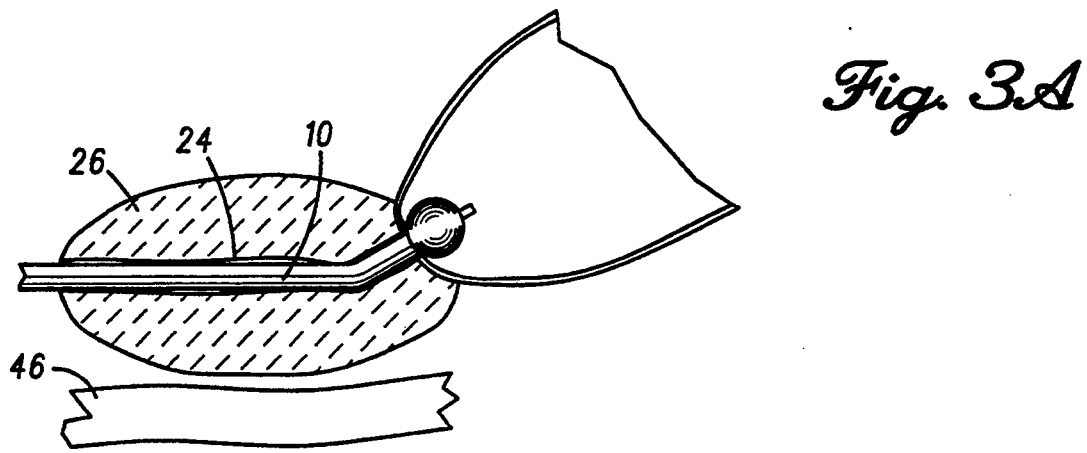
FIG. 3A illustrates the appearance of a naturally curved prostate gland and FIG. 3B illustrates a prostate gland straightened by a thermotherapy device constructed in accordance with the invention.
Figure 3B:
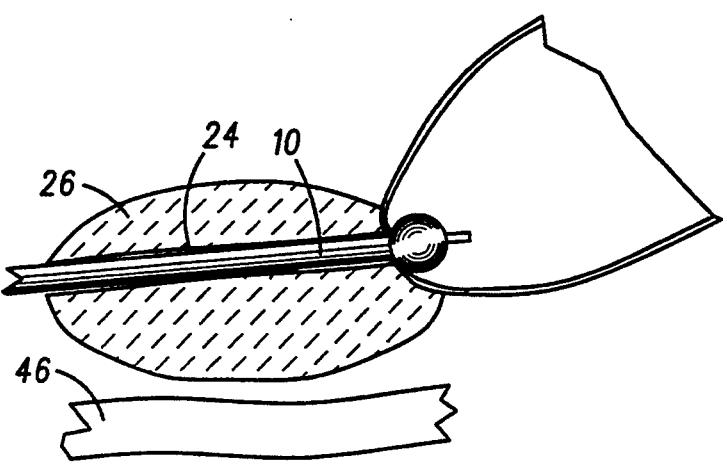
Figure 4:
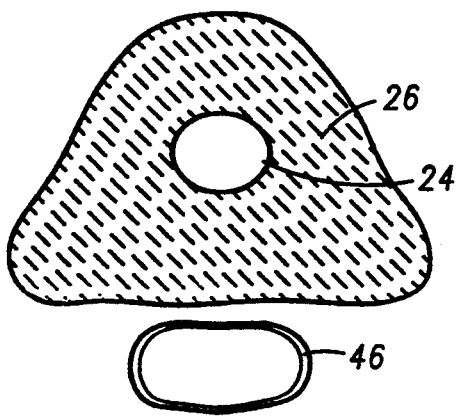
FIG. 4 shows a cross-sectional view of a normal prostate gland, urethra and rectum.

The primary cooling lumen 14 and the secondary cooling lumen 16 can be comprised of a variety of materials including extruded plastics, but are preferably fabricated from a conventional material such as polyethylene terephthalate. This material should preferably have properties resulting in the lumens 14 and 16 being substantially nondistensible, and therefore become substantially rigid when inflated with fluid (liquid or gas) by input into input ends 13 and 15 of the lumens 14 and 16. This rigidity gives rise to several features including the ability to straighten the body passage and surrounding organs into which it is inserted. A nonlimiting example of this feature of the invention shown in FIGS. 2, 3A and 3B is the straightening of the urethra 24 and prostate gland 26 in the thermotherapy treatment of benign prostatic hyperplasia. The lumens can be constructed in a segmented manner as shown in FIG. 3B in phantom to allow selective extension and expansion of the lumens.

As shown in FIG. 3A, the urethra 24 in a normal prostate gland 26 exhibits a curved portion having an angle of approximately 30 degrees. This curved portion of the prostate gland 26 is straightened to the configuration shown in FIG. 3B when the secondary cooling lumen 16 is pressurized to about 30 pounds per square inch with fluid. This straightening action permits treatment of a well-defined geometry, providing a more effective treatment of the prostate gland 26. Such a symmetrical shape allows use of a more predictable energy treatment field. Further, this element of the invention enables the thermotherapy device 10 to be securely anchored by fiction along an extended longitudinal expanse of the walls 28 of the thermotherapy device 10, rather than requiring an anchoring balloon along a narrow length or unstable position, such as those needed for securing prior art devices within body passages. It will be obvious, however, to one skilled in the art that a conventional anchoring balloon can be used in conjunction with the novel device 10 disclosed herein to provide additional anchoring force.

Figure 1B:
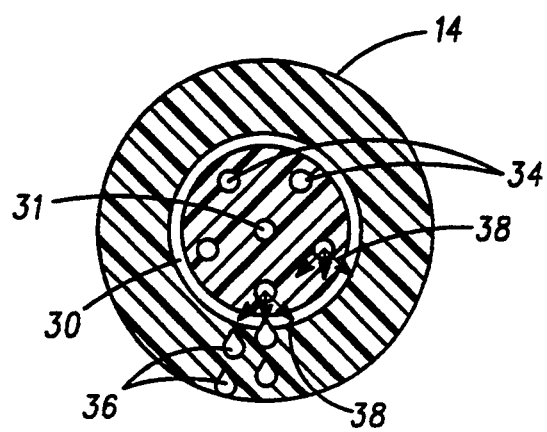
FIG. 1B shows a partial end view of the primary cooling lumen.
Figure 1C:
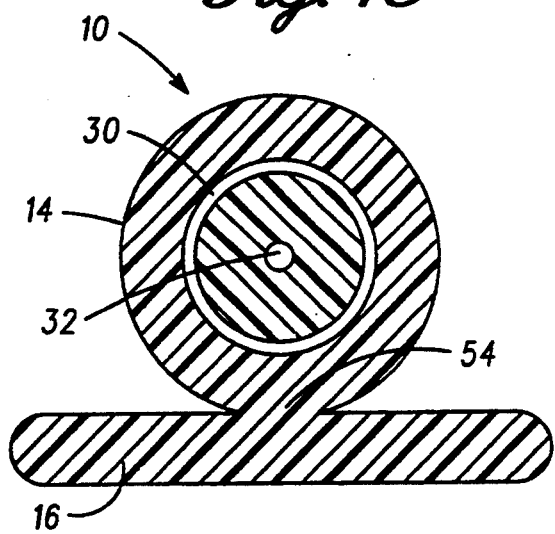
FIG. 1C illustrates an end view of the thermotherapy device.

In the preferred embodiment illustrated in FIGS. 1A, 1B and 1C, a flexible plastic tubing 30 is disposed within the primary cooling lumen 14. An energy source 31 such as an ultrasound transducer 32 is inserted into the plastic tubing 30. Multiple holes 34 are provided at the outlet end of the plastic tubing 30 (see FIG. 1B). These holes 34 enable fluid communication between the interior of the plastic tubing 30 and the interior of the primary lumen 14. Cooling fluid 36 can be pumped through the interior of the plastic tubing 30, whereupon it exits through the holes 34 and enters the primary lumen 14 along flow paths 38, for example (see FIG. 1B).

A number of alternative cooling methods can be utilized with this structure. For example, the cooling fluid 36 entering the primary lumen 14 can be allowed to travel the full length of the primary lumen 14 and back the full length again whereupon it exits through the primary lumen outlet 40, as shown in FIG. 1A. In this embodiment, a separate cooling fluid reservoir and pump (not shown) are utilized to circulate water to the secondary cooling lumen 16. This embodiment allows the secondary cooling lumen 16 to be kept at a significantly lower temperature (or different temperature) than the primary cooling lumen 14.

Alternatively, water entering the primary cooling lumen 14 can be allowed to enter the secondary cooling lumen 16 through a series of holes 42 or a slot 44 (see FIG. 2), or other such openings, disposed along the adjacent perimeter 18 of the primary cooling lumen 14 and the secondary cooling lumen 16. This equalizes the temperature in the two lumens 14 and 16 and provides uniform cooling to the tissues within which the thermotherapy device 10 is inserted.

In another embodiment of the invention, cooling fluid 36 can be pumped first into the secondary cooling lumen 16 as indicated by arrows 45 in FIG. 1A. The cooling fluid 36 can then flow into the primary cooling lumen 14 and the plastic tubing 30 through holes 42 or a slot 44 as shown in FIG. 2.

Various pressures and flow volumes of the cooling fluid 36 can be provided to the thermotherapy device 10. In the treatment of benign prostatic hyperplasia, experiments have shown that exceptional cooling can be provided from applying pressures of 30 to 265 pounds per square inch at circulating volumes of 100 to 100 milliliters per minute. It will be obvious to one skilled in the art that different cooling methods, cooling fluids and cooling fluid volumes and pressures can be utilized effectively. Further, it will be obvious to one skilled in the art that heat or radiation sources other than the ultrasound transducer 32 described for energy source 31 can be equally suitable for proposed treatments (thermotherapy or hyperthermia, though for the purposes of determining the scope of the claims, "thermotherapy" is considered to include hyperthermia treatment). For example, a microwave antenna can be used to deliver the radiant energy as the energy source 31. Alternatively, a laser light guide such as the structure disclosed in U.S. Pat. No. 4,878,725 (Hessel, et al.) is a satisfactory energy source 31 when used in conjunction with a laser-transparent lumen material.

The asymmetric structure of the thermotherapy device 10 provides significant improvements over the substantially symmetric devices. As a nonlimiting example, use of the improved thermotherapy device 10 for the treatment of benign prostatic hyperplasia will be described and shown herein.

Referring to the figures, and more particularly to FIG. 2, the thermotherapy device 10 is shown inserted transurethrally into the human prostate gland 26. As shown in FIGS. 2–7, the rectal wall 46 can be located close to the urethra 24 as the device 10 passes through the prostate gland 26.

High temperatures in the rectal wall 46 can be caused by treatment of benign prostatic hyperplasia and can severely limit the duration and effectiveness of the treatment. As discussed previously, thermotherapy requires higher temperatures generally to be maintained at the abnormal tissue compared to conventional hyperthermia treatments. Accordingly, shielding of the rectal wall 46 is even more critical than when performing a hyperthermia treatment.

Figure 5:
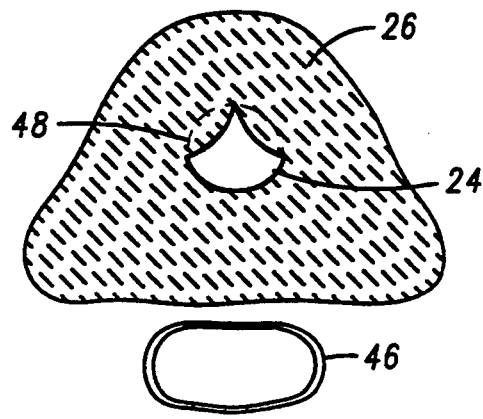
FIG. 5 illustrates a cross-sectional view of a diseased prostate gland impinging upon the urethra.

Further, as shown in FIGS. 5–7, the transitional zone 48 of the prostate gland 26 is the primary source of tissue impinging upon the urethra 24. This impingement causes difficult urination due to the restricted diameter of the urethra 24. This can cause serious kidney problems and extreme discomfort. The asymmetric structure of the present invention enables application of the radiation to the prostate gland 26 to be preferentially directed to the diseased tissue (such as, the transitional zone 48 in FIG. 5), giving rise to more effective treatment with thermotherapy, while also preventing tissue damage, such as damage to the rectal wall 46.

As shown in FIG. 6, use of a symmetrical applicator 50 for treatment results in the applicator being relatively close to the rectal wall 46. The ultrasound transducer 32 in the applicator 50 can produce an energy field which is symmetric about the applicator's longitudinal axis. High temperatures for the rectal wall 46 can arise from application of energy and therefore cause reduction of the duration and effectiveness of the treatment of the transitional zone 48 of the prostate gland 26. As shown in FIG. 7, the asymmetric structure of one embodiment of the thermotherapy device 10 physically shifts the ultrasound transducer 32 toward the transitional zone 48 and away from the rectal wall 46 by dilating (compressing) the overlying and impinging prostate tissue zone 48 of the prostate gland 26.

The asymmetric structure of the thermotherapy device 10 allows high intensity energy to reach the transitional zone 48 of the prostate gland 26, while substantially preventing high intensity ultrasound energy from reaching the rectal wall 46. Accordingly, more effective thermotherapy treatment of benign prostatic hyperplasia can now be provided with the present invention. Such treatment can be provided without high rectal wall 46 temperatures and attendant damage which severely limits the effectiveness of prior art designs. Additionally, the ultrasound transducer 32 can produce an asymmetric and/or focused energy pattern to completely shield the rectal wall 46 from high treatment temperatures. These transducer configurations are discussed in greater detail below.

In the form of the invention using a laser device as the energy source 31, a light reflective or absorptive fluid or substance can be used in (or on) a cooling chamber to effectively screen the rectal wall 46 from high intensity energy. The form of the invention using an ultrasound type of energy source 31 can utilize a sound reflective or absorptive fluid or substance in (or on) a cooling chamber for high intensity energy screening purposes.

In another form of the invention, a radioreflective form of the fluid 36 can be flowed through the secondary cooling lumen 16 to effectively screen the rectal wall 46 from high intensity microwave energy. Another variation on this concept is the use of radiation absorptive fluids 36 in the secondary cooling lumen 16 to screen the rectal wall 46. Another variation is the use of a radioreflective or radiation absorptive substance to form a lining on at least a portion of a cooling chamber to provide the desired screening effect.

Figure 17:
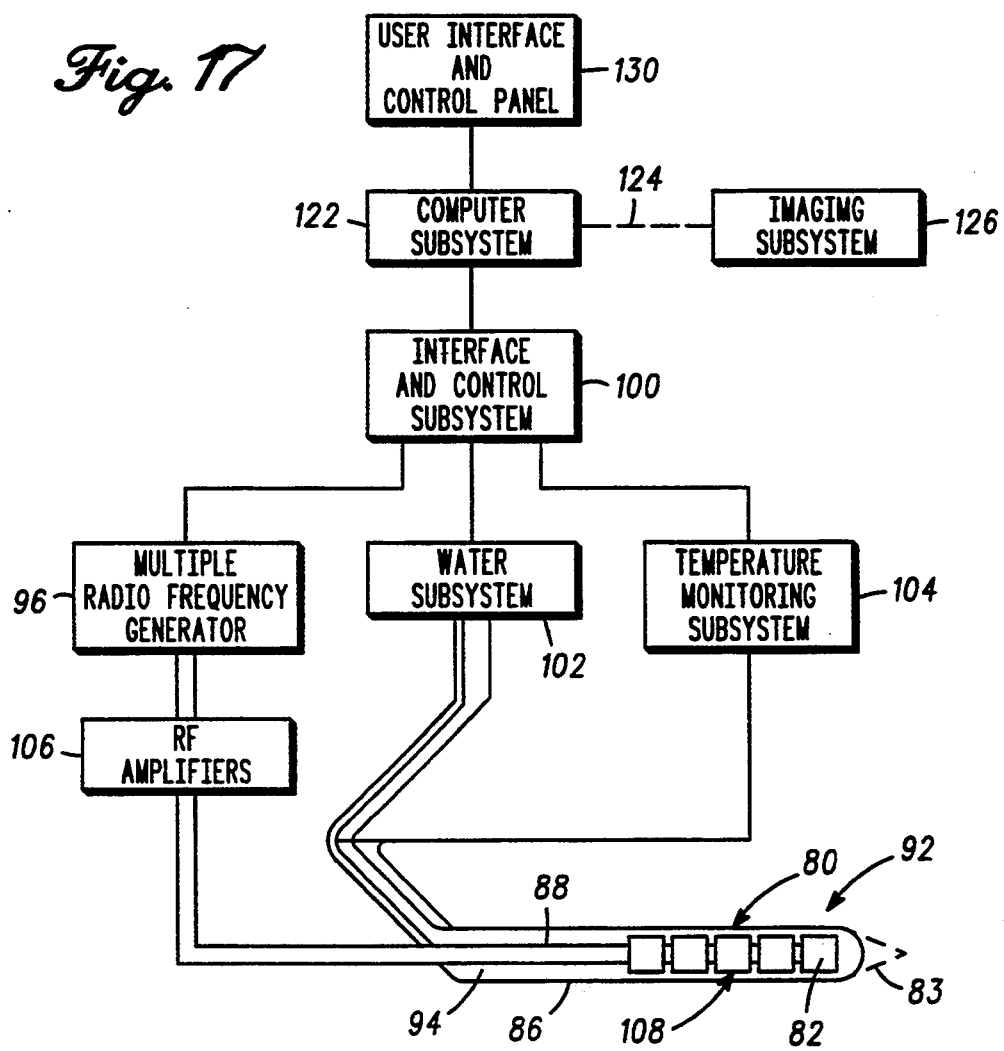
FIG. 17 illustrates a schematic view of an ultrasound applicator system constructed in accordance with the invention.
Figure 18:
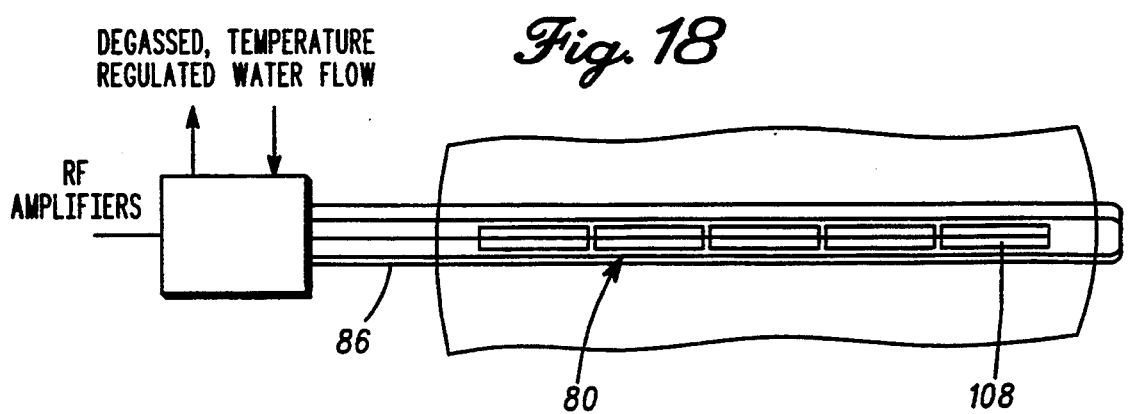
FIG. 18 shows a simplified schematic of an ultrasound applicator and delivery system.

Yet another embodiment of the invention allows interstitial insertion of the thermotherapy device 10 and/or delivery system 92 for thermotherapy treatment of tissues which are not located in close proximity to normal body openings or channels. In this embodiment, the thermotherapy device 10 can be inserted into a conventional rigid probe (such as a catheter) that is provided with a pointed insertion tip 83 as shown in FIG. 17. The small diameters of the ultrasound embodiments described herein are particularly useful for interstitial insertion.

In another form of the invention the primary cooling lumen 14 and/or the secondary cooling lumen 16 can be a single balloon (as shown in FIG. 1C) with a thin liquid barrier 54. The shapes of the lumens 14 and 16 can be modified to provide the desired path length of cooling fluid 36 (and path length of radiation absorber or reflector) seen by energy emanating from the ultrasound transducer 32 (or other suitable energy source). The cooling fluid 36 can comprise an energy absorber or reflector to enable the clinician to have the ability to construct a desired heating pattern to maximize treatment of disposed tissue and minimize harm to normal tissues.

In another form of the invention the device 10 includes two secondary cooling lumens 16 and 16' as shown in FIG. 10. The additional secondary cooling lumen 16' is attached in the same manner as previously disclosed for the first secondary cooling lumen 16. Further, the alternative cooling paths and shielding means for the two lumen devices are readily adaptable to the three lumen configuration by one skilled in the art.

This configuration with three lumens adds several advantages over the two lumen configuration disclosed herein. The additional secondary cooling lumen 16 allows greater flexibility in matching the geometry of many prostate glands. In some prostate glands 26, the urethra 24 does not pass through the center of the prostate gland 26, but is off-set in a direction toward nontarget tissue. While the two lumen configuration previously disclosed can correct for prostate glands 26 in which the urethra 24 passes closer to the rectal wall 46, the addition of the second secondary cooling lumen 16 enables more efficient and selective treatment of those prostate glands 26 which contain the urethra 24 passing closer to the anterior portion of the prostate gland 26. Without the second secondary cooling lumen 16, the anterior-most portions of the prostate gland 26 can be overheated prior to the rectal wall 46 temperature reaching harmful levels. This can result in injury to the outer capsule of the gland and can lead to complications such as fistula creation between the urethra 24 and the perineum, sepsis and peritonitis. Alternatively, thermotherapy treatment power levels must be decreased for such prostate glands 26 with the urethra 24 passing closer to the anterior portion of the prostate gland 26. In some patients, the location of the urethra 24 can exclude them from treatment with devices other than the three lumen configuration device.

The three lumen configuration of the thermotherapy device 10 will also orient itself within the prostate gland 26 as previously described for other embodiments of the invention. Additionally, the anchoring forces for the thermotherapy device 10 are further improved by the greater surface area provided by the additional secondary cooling lumen 16.

Another embodiment of the present invention utilizes a temperature sensor 56 embedded in a cooling lumen at the tip or along the primary lumen 14 midway along the energy source 31 of the thermotherapy device 10 as shown in FIG. 1A. Alternatively, the temperature of the output temperatures of the cooling fluid 26 have been determined to track the nontarget tissue temperature and can therefore be used to control the treatments.

Figure 11:
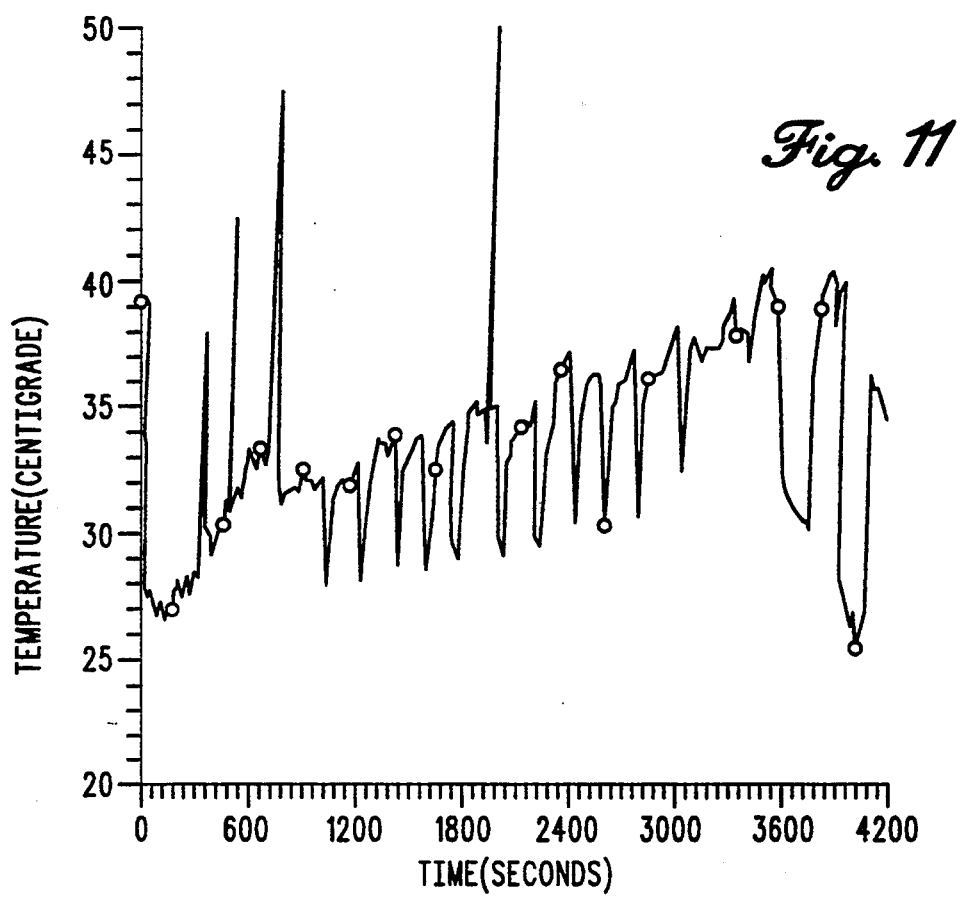
FIG. 11 illustrates temperature readings from a urethral sensor over time.
Figure 12:
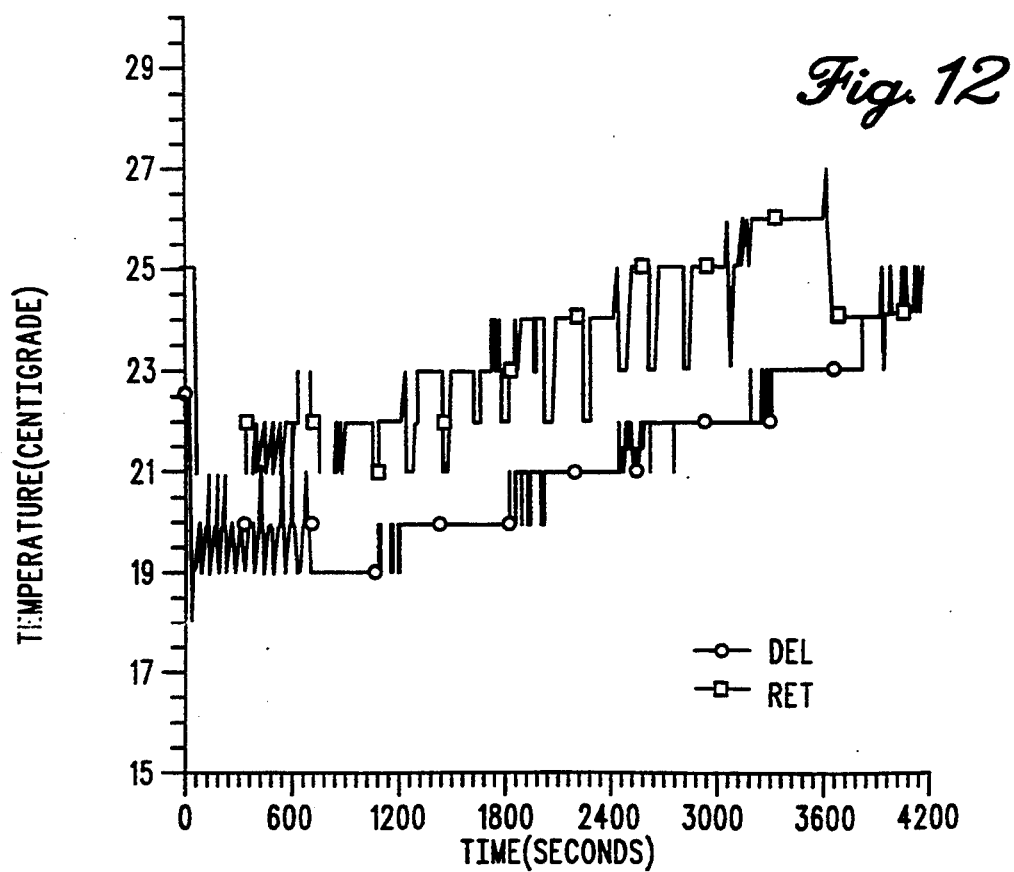
FIG. 12 shows temperature readings from a remote temperature sensor over time.
Figure 13:
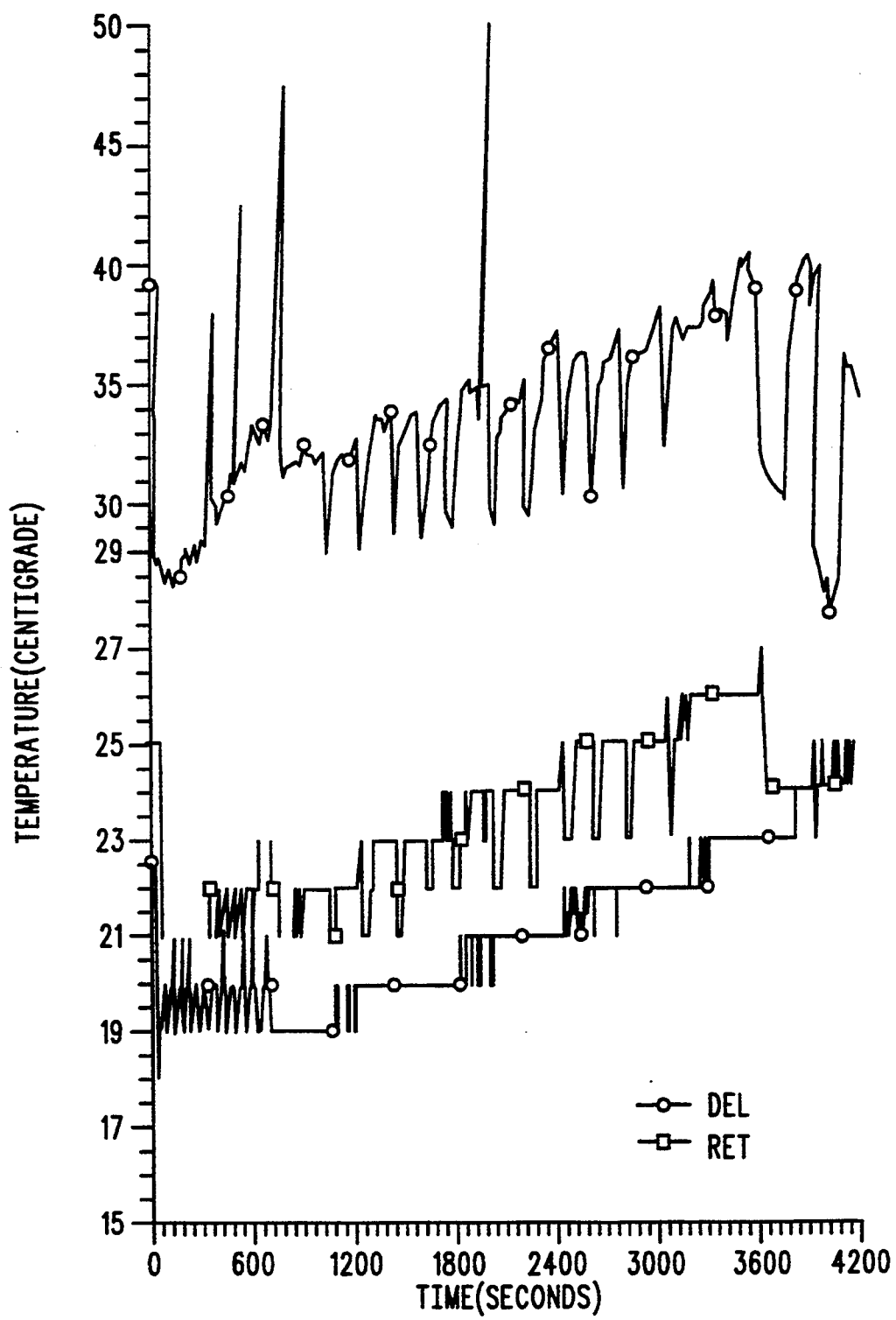
FIG. 13 illustrates a temperature versus time plot produced by superimposing FIGS. 11 and 12.

Referring to FIGS. 11–13, data collected from animal experiments shows a surprisingly good direct correlation between the output temperatures of the cooling fluid 36 and the urethral wall temperatures as monitored by urethral wall temperature sensor. It will be apparent to one skilled in the art that sensing input and output cooling fluid 36 temperature differentials or other remote temperature sensing methods can also satisfactorily control the treatments. The remote temperature sensing configuration exhibits sufficient sensitivity and can be correlated with patient pain thereby enabling better control.

Figure 14:
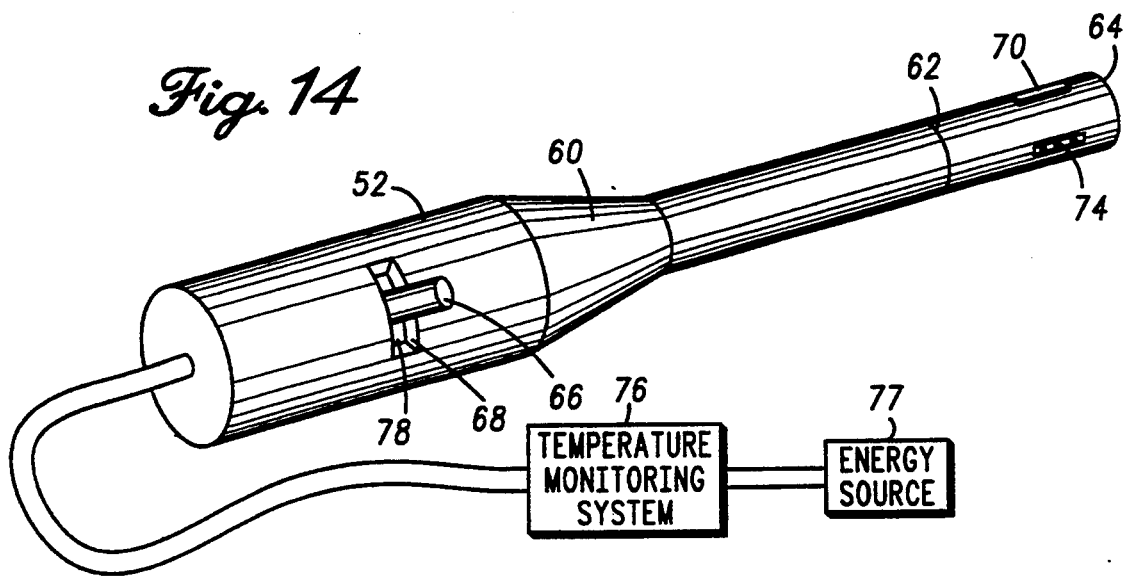
FIG. 14 shows a perspective view of a transrectal probe constructed in accordance with one form of the invention.
Figure 15:
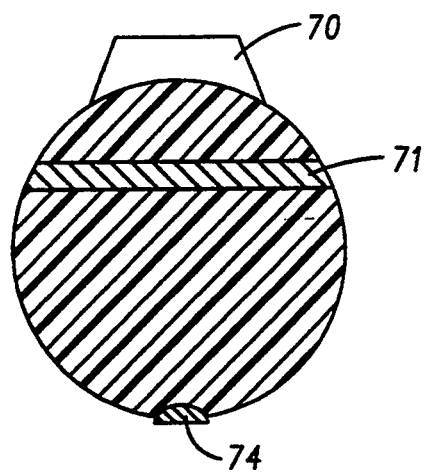
FIG. 15 illustrates a cross-sectional end view of the transrectal probe shown in FIG. 14.

Referring to FIGS. 14 and 15, another embodiment of the present invention utilizes a transrectal device 52 providing temperature feedback to a temperature monitoring system which controls the energy output of the thermotherapy device 10.

The transrectal device 52 includes a handle portion 60, a rotational joint 62, and a rotating end 64 as shown in FIG. 14. Handle portion 60 of the transrectal device 52 includes a lever 66 which is attached to a portion of rotating end 64 that is disposed within the interior of the handle 60. A slot 68 is provided in the handle portion 60 so that lever 66 can rotate about the perimeter of the handle portion 60. Because lever 68 is attached to a portion of rotating end 64, pivoting the lever 66 in the slot 68 rotates the rotating end 64 coordinately.

Rotating end 64 includes an ultrasound transducer 70, a replaceable array of preferably copper-constantin thermocouple 74, and energy shielding material. As shown in FIGS. 14 and 15, the thermocouple 74 is offset from the ultrasound transducer 70. Though various angles of offset can be used, preferably the thermocouple 74 is one hundred eighty degrees from the ultrasound transducer 70 as shown in FIG. 15. Alternatively (as shown in FIG. 14) the angle of offset can be ninety degrees. This angle of rotation necessitates a slot 68 extending through at least ninety degrees of the perimeter of the handle 60.

Though the transrectal device 52 can be used with other structures, when used in conjunction with the thermotherapy device 10, combined ultrasound guided positioning of the thermotherapy device 10 and rectal wall temperature monitoring are provided by a single device. Materials can be inserted or applied to the thermotherapy device 10 to render it more visible to ultrasound detection.

The novel structure of the transrectal device 52 minimizes possible effects of energy applied for therapy on the ultrasound transducer 70 by shielding the ultrasound transducer 70 from such energy with shielding material 71. Before energy can be applied to the prostate, the portion of the rotating end 64 containing the thermocouple 74 must be rotated so it is facing the thermotherapy device 10 in its inserted position in the urethra 24. Feedback from the thermocouple 74 is provided by conventional wiring to a temperature monitoring system 76 which turns off the thermotherapy energy source 77 when the desired temperature range is exceeded.

When positioning information is desired, the lever 66 is rotated in the slot 68 so that the ultrasound transducer 70 is facing the thermotherapy device 10 in an inserted position. Lever 66 also includes an electrical switching portion 78 which turns the thermotherapy energy source 77 off when the ultrasound transducer 70 is a position facing tie thermotherapy device 10. In this way, the structural integrity of tie ultrasound transducer 70 is maintained.

Figure 16:
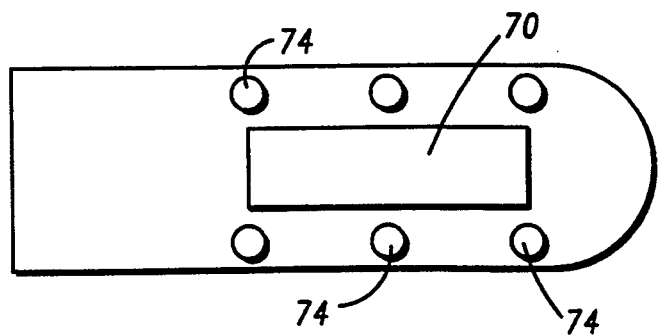
FIG. 16 shows a top view of an alternative embodiment of a transrectal probe.

Alternatively, a probe using thermocouples 74 and an ultrasound transducer 70 arranged in tie manner shown in FIG. 16 can be used to provide temperature and positioning feedback. Further, it will be apparent to one skilled in the art that alternative temperature sensors such as thermistors, fiber optic-based systems or otter conventional temperature sensors can be readily substituted for the thermistors 74.

Another preferred embodiment of one form of the invention is shown in FIGS. 17, 18 and 23–26. This embodiment comprises a longitudinally arranged array 80 of cylindrical concave sections 82, each of which can produce a line focus 84 and which can be rotated within a catheter insertion means 86. The array 80 is arranged within a thin-walled flexible hollow tube 88 which can be rotated by tie operator. This entire assembly 90 can be located within a catheter delivery system 92 with an intraluminal flow of degassed water 94. These cylindrical concave sections 82 can be driven independently of each other by multiple radio frequency generators 96 controlled by an interface and control subsystem 100. It will be apparent to one skilled in the art that conventional catheter delivery systems as well as tie device 10 and delivery systems 92 described herein can be used satisfactorily.

It is possible to configure tie ultrasound transducers to yield a small diameter configuration. These small diameter structures are particularly useful for the interstitial embodiments described herein, providing increased treatment flexibility. These structures can be inserted via hypodermic needles or catheter means. Further, a plurality of these interstitial devices can be inserted to simultaneously treat multiple tissue regions.

As shown in FIG. 17, the interface and control subsystem 100 can receive input and can provide an output to multiple radio frequency generators 96, a water subsystem 102 and a temperature monitoring system 104. The multiple radio frequency generators 96, in conjunction with RF amplifiers 106, provide power to the ultrasound transducers 108 such as, for example, cylindrical concave sections 82. The water subsystem 102 provides a flow of degassed water 94 or a static volume to the catheter delivery system 92 and can also monitor and vary the water temperature and volume delivered. The temperature monitoring system 104 can monitor the patient's tissue temperature through ultrasound interrogation, direct temperature of measurement or other methods and can also monitor the temperature of the water subsystem 102 if needed. The interface and control subsystem 100 is controlled by the computer subsystem 122 which also receives input 124 from the imaging subsystem 126 which can be connected to the transrectal device 52 described herein or other imaging devices. The computer subsystem 122 is controlled by a user interface control panel 130 to allow precise and intuitive control of the system functions. Each of the ultrasound transducers 108 in an array 80 can be individually controlled by the use of the components described above.

Figure 19A:
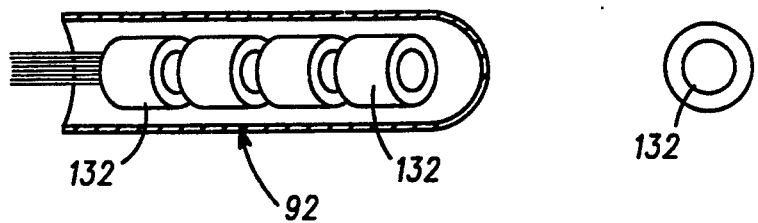
FIG. 19A show perspective and end views of an ultrasound thermotherapy probe including an array of cylindrical transducers.
Figure 19B:
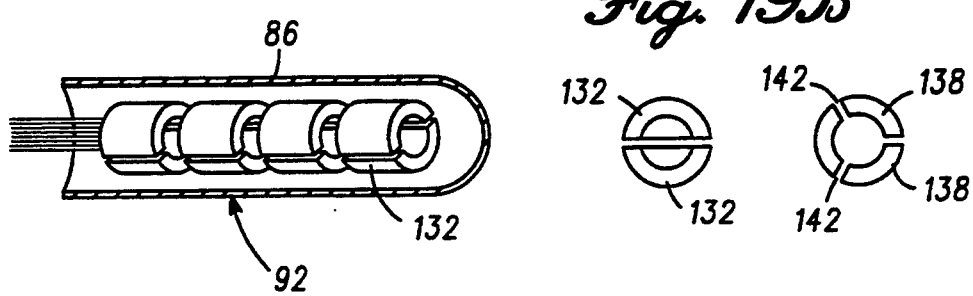
FIG. 19B illustrates a perspective view and two end views of an ultrasound thermotherapy probe having an array of segmented cylindrical ultrasound transducers.
Figure 19C:
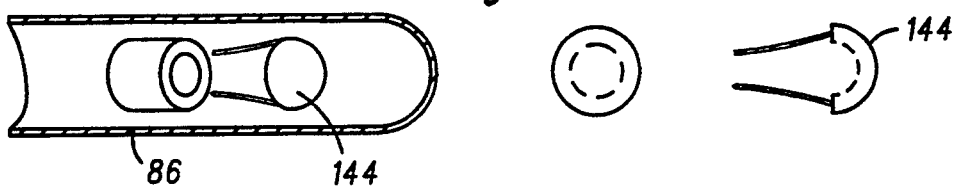
FIG. 19C shows a side view and end view of a hemispherical transducer used for an end cap structure for an ultrasound thermotherapy probe.

In another form of the invention shown in FIG. 19A, an array 80 of substantially cylindrical transducers 132 can be arranged in series 134 in a delivery system 92. These cylindrical transducers 132 produce a substantially symmetrical energy field about the catheter delivery system 92. As shown in FIG. 19B, the cylindrical transducers 132 can be segmented into 180° portions, 120° portions or into other portions as desired. Alternatively, segments 138 having different angular dimensions can be used to create "dead zones" where no ultrasound energy is transmitted. As a nonlimiting example, a dead zone produced by a gap 142 between segments 138 can be used to prevent ultrasound energy from heating the rectal wall 46 or other tissue during a thermotherapy treatment.

Using the systems described above, it is further possible to control each of the segments 138 individually, thus allowing precise tailoring of the energy field to the shape of the tissue to be treated. A hemispherical end cap transducer 144 can be used in conjunction with the above-described embodiments or individually in order to produce a diverging energy field at the end of the delivery system 92. This structure can be particularly useful for an interstitial embodiment of the present invention.

Figure 19D:
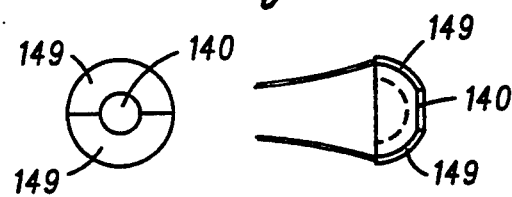
FIG. 19D illustrates an end view and a side view planar/spherical end cap structure for use with an ultrasound thermotherapy probe.
Figure 20A:
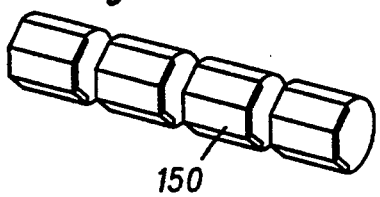
FIGS. 20A and 20B show a perspective view and an end view, respectively, of an alternative embodiment of an ultrasound thermotherapy probe constructed in accordance with the invention.
Figure 20B:
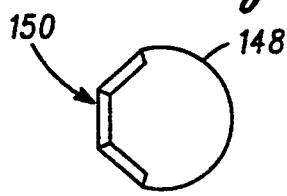

As shown in FIG. 19D, a planar segment 140 and spherical segments 149 can be used to roughly approximate a cylindrical shape and achieve a cylindrical energy distribution. The hemispherical end cap transducer 144 of substantially hemispherical design described above can be used in conjunction with this embodiment as well (not shown). Alternatively, a multisegmented planar-cylindrical array 150 (as shown in FIG. 20) can be used in conjunction with a rotatable component of a delivery system 92 to focus an energy field upon tissues to be treated. This focusing allows precise application of the ultrasound energy for more effective treatment.

Figure 21:
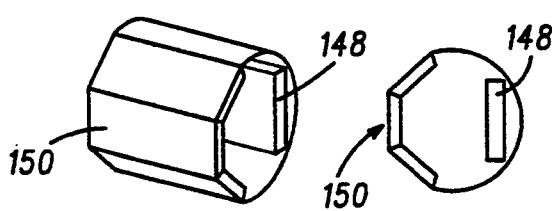
FIG. 21 illustrates a perspective view and an end view of another alternative embodiment of an ultrasound thermotherapy probe having a rotatable diagnostic linear phased array.
Figure 30:
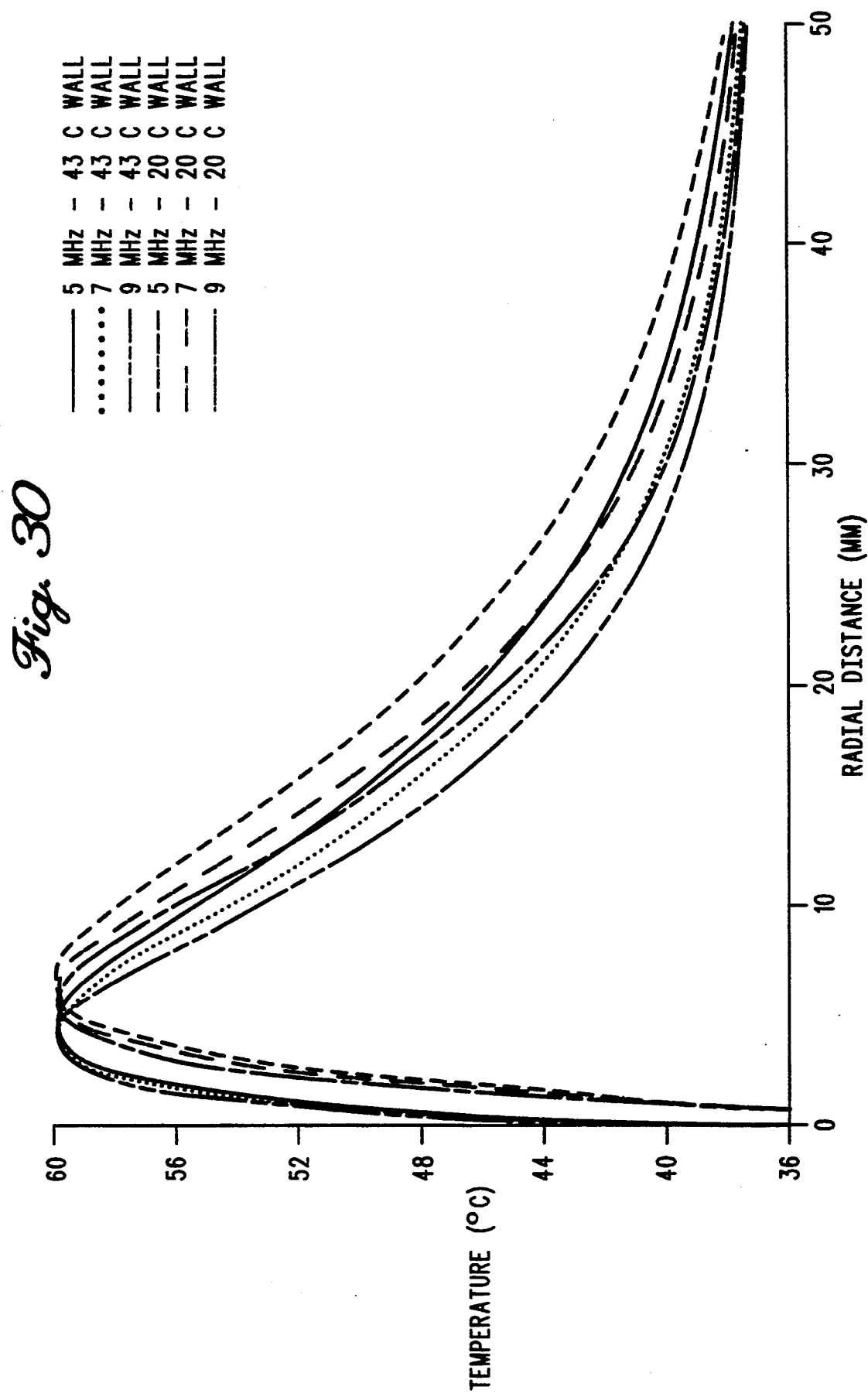
FIG. 30 illustrates simulated radial temperature profiles at different ultrasonic frequencies produced by cylindrical transducers.

Further, a diagnostic linear phased array 148 (shown in FIG. 21) can be integrated with the multi-segmented planar-cylindrical array 150 to assess the temperatures associated with the treatment. By rotating the diagnostic based array 148 to interrogate where the tissues which had been treated, noninvasive temperature sensing can be accomplished or, alternatively, an imaging function can be performed. These functions are described in greater detail below.

FIG. 22 illustrates a sample delivery system 92 which can be used in accordance with the various embodiments of the invention described above. For illustrative purposes, cylindrical transducers 132 are shown as a nonlimiting example. The cylindrical transducers 132 can be connected to each other and to support tube 88 by silicon adhesive. Small wires 156 carrying RF energy to each cylindrical transducer 132 can be nm along the inner support tube 160. Attentively, the wires 156 can be relocated for specific design considerations. Although various transducers can be used, in the preferred embodiments illustrated in FIGS. 19–25, ultrasound transducers of PZT-4 or PZT-5 operating at a frequency of between 5 MHz and 9 MHz perform satisfactorily.

Figure 31:
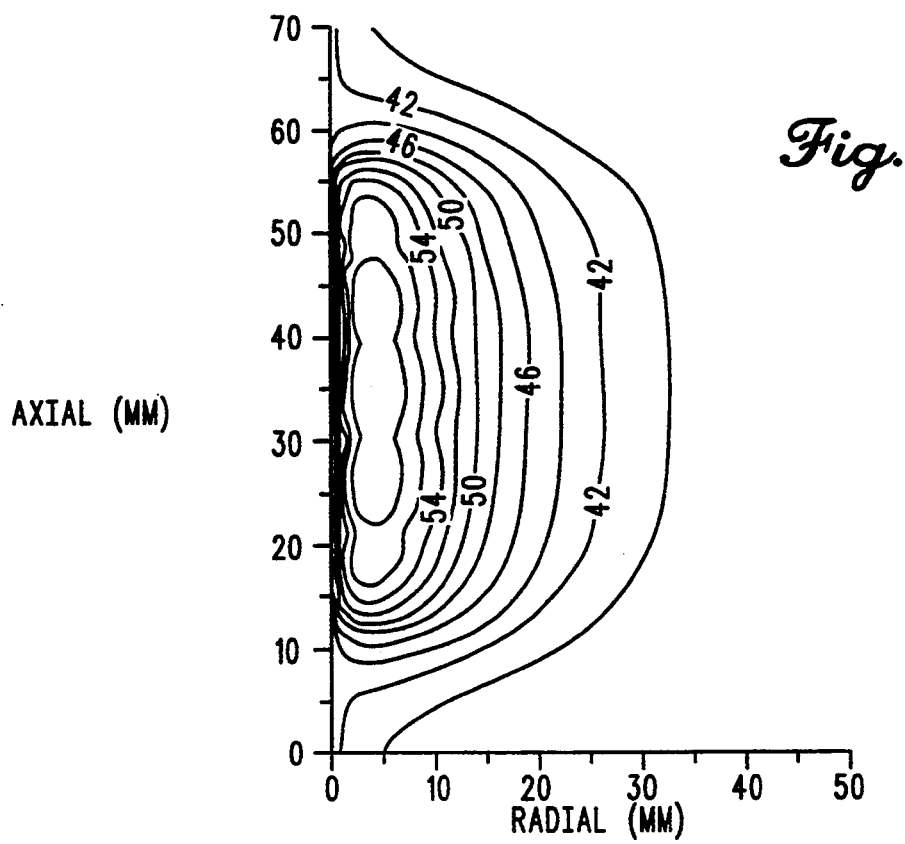
FIG. 31 shows computed temperature distributions from a five element ultrasound thermotherapy probe with all elements being powered.
Figure 32:
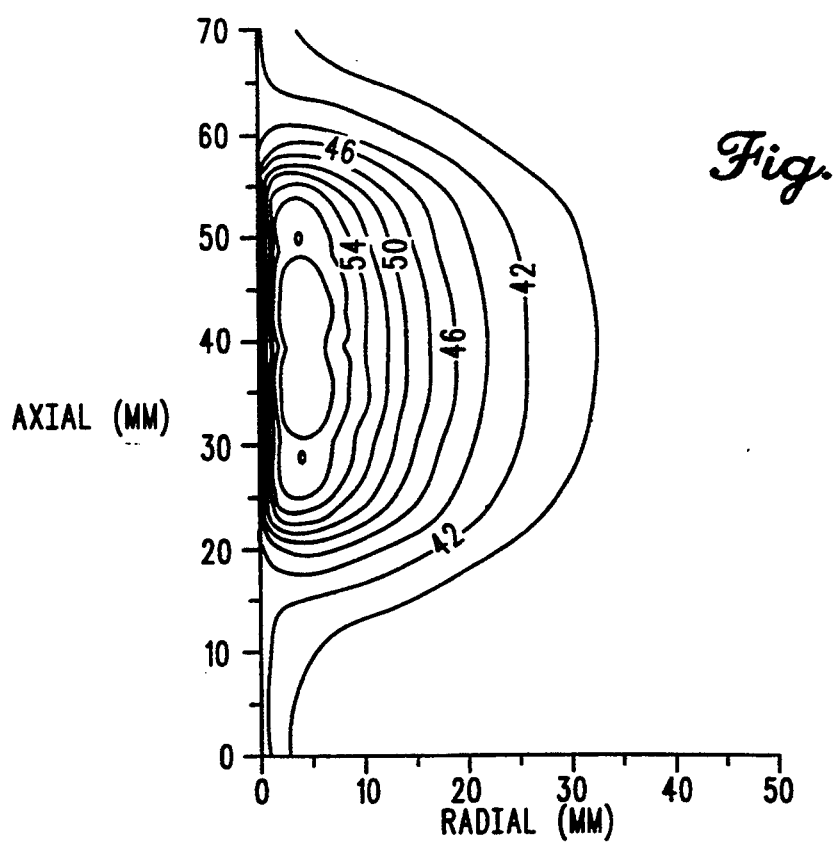
FIG. 32 illustrates computed temperature distributions from a five element ultrasound thermotherapy probe having all elements but one end element being powered.
Figure 33:
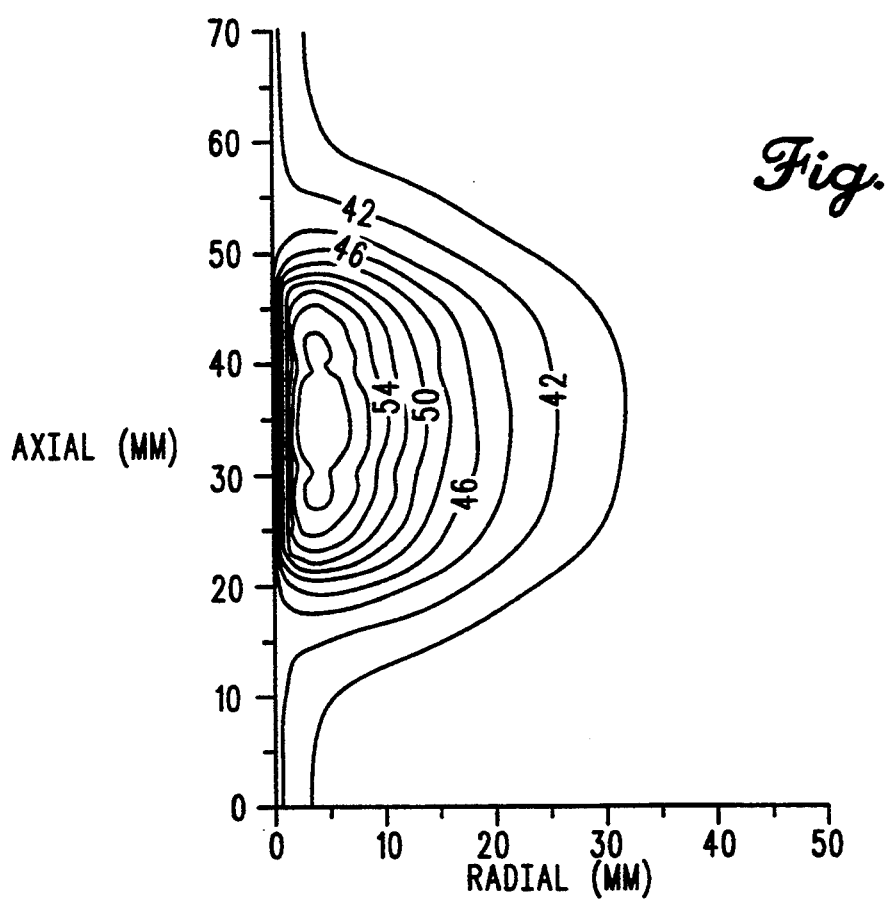
FIG. 33 shows computed temperature distributions from a five element ultrasound thermotherapy probe with both end elements remaining unpowered.

Exemplary temperature profiles are illustrated in FIGS. 30–33. These profiles show the desirable therapeutic effects of one embodiment of the invention. Further, FIG. 31 illustrates how frequency variance directly affects the depth of treatment. Thus, frequency changes can be used in conjunction with or in place of inflatable lumens for relatively small adjustments in treatment depth. In addition to driving the transducers at separate discrete frequencies, the transducers can also be driven by "sweeping" the driving frequency over a narrow frequency band. This technique decreases efficiency slightly, but provides a smoother energy pattern.

FIG. 23 shows a transducer assembly 164 for a rotating cylindrical line-focus design. Arcuate ultrasound transducers 158 with a radius of curvature 166 larger than the delivery system radius of curvature 152 are mounted within the delivery system 92. Preferably, the longitudinal axes of the arcuate ultrasound transducers 158 are oriented parallel to the longitudinal axis 22 of the delivery system 92. The delivery system 92 preferably comprises a transducer support tube 162 capable of carrying water 168 for cooling the patient's tissue adjacent the delivery system 92 and also can be used for cooling the energy source 31. It should be noted that the arcuate ultrasound transducers 158 generally require little or no cooling for effective performance. Other energy sources 31 such as microwave antennae can require substantial cooling for optimal performance.

As an illustrative, nonlimiting example, each arcuate ultrasound transducer 158 can be a partial cylinder of 8.5 mm radius of PZT-4 or PZT-5 material. Small wires 156 carrying the RF power to each arcuate ultrasound transducer 158 can be run along the longitudinal edge 174 of each transducer assembly 164. Optionally, a backing material 176 (as shown in FIGS. 23B and 23C) can be used in the transducer support tube 162 to further support the arcuate ultrasound transducers 158 and to increase their bandwidth. Alternatively, matching layers of the material can be added to the concave face of the transducers 158 to improve power transfer.

A preferred embodiment of this form of invention (shown in FIGS. 24–26) comprises four arcuate ultrasound transducer elements 158 arranged linearly with the concave portion of each transducer 158 focusing the energy radially away from the longitudinal axis 178 of the transducers 158 at a fixed focal zone distance 180. Each arcuate ultrasound transducer 158 is preferably PZT-4 or PZT-5 polarized ceramic material having a radius of curvature between 1 cm and 1.5 cm which is cut in cylindrical cross section to a maximum of 5 mm. (The four transducer elements have a longitudinal dimension of between 5 mm and 10 mm each.)

The focal region 182 of each arcuate transducer 158, illustrated in FIGS. 24A and 24B, is "cigar-shaped" in the radial direction extending from a distance of approximately 5 mm to 15 mm (inside the prostate 26, for example, as measured from the urethral wall 184) and approximately 4–10 mm in width. Longitudinally, the shape of the focus is a "line focus" with the focal region width being approximately 4 mm and the depth of focus approximately 12 as shown in FIG. 24B. This focal region 182 enables precise application of the energy which can greatly increase the effectiveness of the thermotherapy treatment.

The four transducers are arranged as shorten in FIG. 25 and can be mounted in a flexible plastic transducer support tube 162 (or sheath), with all wiring connections to the transducers being made inside the robe 162 along the back (convex) side of the transducers. A cross-sectional view of the mounting technique is shown in FIGS. 24 and 26. The placement of the applicator 50 in the urethra 24 is illustrated in FIGS. 27–29. Zones 188 of prostatic tissue destruction within the prostatic lobes 190 are shown in the longitudinal cross-sectional view in FIG. 27. Lateral and median lobe zones 188 of prostatic tissue destruction are shown in cross section in FIG. 28.

The applicator 50 is operated by inserting the transducer support robe 162 and the arcuate ultrasound transducers 158 into the urethral catheter delivery system 92 to the appropriate position whereby the transducers are positioned within the urethra 24. The desired prostatic tissue damage zones are created by rotating the transducer support robe 162 and the arcuate ultrasound transducers 158 within the delivery system 92 to appropriately position the focused energy within each of the prostatic lobes. Additionally, the multi-lumen delivery systems previously described can be used to control the depth of the damage zones at each rotational position. Inflating one or more lumens can move the energy source 31 closer or farther away from selected tissues, thereby providing precise control of the energy application.

Positioning is based upon a transrectal diagnostic ultrasound scan taken just prior to treatment which is used to locate the transducer array within the prostate 26 and to locate the position of the prostatic lobes. A compass index 196 is provided at the insertion point of the transducer support robe 162 and the arcuate ultrasound transducers 158 into the delivery system 92 which is used to position the direction of the focus beam within the lobes of the prostate 26. Further, FIG. 29 illustrates a delivery system 92 within a human body, showing the graduations 196 on the delivery system 92 which allows ready inspection of the depth to which the delivery system 92 has been inserted. A transrectal diagnostic probe 198 is also illustrated. Different intensifies of energy can be applied to produce different reproducible degrees of therapeutic effect.

Positioning can be continued using either diagnostic ultrasound or cystoscopy. This novel thermal therapy applicator provides the ability for ablative therapy of selected volume-controllable regions of the prostate 26 while preserving the urethra 24 and avoiding sphincters, nerves, blood vessels and other structures.

Yet another preferred embodiment of the subject invention includes the capability for temperature sensing using the same ultrasound transducer elements that are used for therapy. The manner is which this is accomplished is to further divide the elements of the arrays shown in, for example, FIGS. 22–26 into sub-elements which are each separately wired to the instrumentation. During therapy, the sub-element sections are electronically connected together and therapeutic RF power levels applied to each element in its entirety, yet each element is driven independently by its own RF generator. Within the course of a therapy session, RF power can be briefly interrupted momentarily at various time-points and the elements electronically separated into sub-elements and connected to an RF pulser-receiver which permits measurement of the acoustic wave velocity within the tissue treatment volume at multiple points. In this manner, one sub-element can be pulsed and the remaining sub-elements used to receive the return signal, with the time delay of the return signal being temperature-dependent. Thus, the same volume is interrogated that is treated.

Another preferred embodiment of the present invention utilizes the sub-elements and the pulser-receiver with the addition of video signal processing to produce ultrasound images of the tissue being treated. This is based on the same concept as linear array ultrasound imager, except that the same array elements/sub-elements used for this purpose are used for the therapy.

While preferred embodiments have been illustrated and described, it should be understood that changes and modifications can be made therein without departing from the invention in its broader aspects. Various features of the invention are defined in the following claims.

What is claimed is:

1. A method of providing thermal therapy to prostate tissue of a patient, comprising:
    providing a substantially cylindrical ultrasound transducer for producing an energy field focused along a line;
    locating said substantially cylindrical ultrasound transducer substantially within an applicator housing, said substantially cylindrical ultrasound transducer being dimensioned to have a radius of curvature larger than a radius of curvature of said applicator housing; and
    providing a power source for said ultrasound transducer to produce the line focused energy field for providing said thermal therapy to prostate tissue of a patient.

2. The method as defined in claim 1 wherein said cylindrical ultrasound transducer is disposed with its cylindrical axis substantially parallel to the longitudinal axis of said applicator housing.

3. The method as defined in claim 1 wherein said applicator housing comprises a plurality of lumens.

4. The method as defined in claim 3 wherein at least one of said lumens is nondistensible.

5. The method as defined in claim 1 wherein said cylindrical ultrasound applicator comprises a plurality of transducers focused at selected locations.

6. The method as defined in claim 5 further including an additional ultrasound transducer comprised of a planar transducer.

7. The method as defined in claim 1 further including means for performing ultrasound imaging for monitoring at least one of tissue damage from the thermal therapy and location of said applicator housing.

8. The method as defined in claim 1 further including means for cooling said ultrasound transducer.

9. A method of applying thermal therapy to a tissue region of a patient, comprising the steps of:
    inserting an applicator housing near said tissue region;
    placing a substantially arcuate ultrasound transducer having a radius of curvature greater than a radius of curvature of said applicator housing and being capable of rotation in said applicator housing;
    supplying energy to said arcuate ultrasound transducer and producing a converging energy pattern distributed substantially along a line; and
    rotating said arcuate ultrasound transducer to position said converging energy line pattern upon tissue to be treated.

10. The method as described in claim 9 further including the step of providing cooling of said transducer.

11. The method as described in claim 9 further including another transducer for applying nonline patterns of ultrasound energy.

12. A method of producing a focused ultrasound energy pattern, comprising the steps of:
    determining a distance between a tissue region to be treated and an access path in said patient;
    selecting a substantially arcuate ultrasound transducer having a first radius of curvature generally corresponding to said distance;
    inserting said arcuate ultrasound transducer into an applicator having a smaller radius of curvature than said first radius of curvature; and supplying energy to said arcuate ultrasound transducer to produce a converging energy pattern distributed substantially along a line.

13. The method as described in claim 12, further including the step of rotating said arcuate ultrasound transducer to focus said converging energy pattern upon the tissue region to be treated.

14. The method as described in claim 12, wherein a plurality of ultrasound transducers can be used to focus a plurality of converging energy patterns on the tissue region to be treated.

15. A method for providing thermal therapy to a tissue region of a patient, comprising the steps of:
providing a primary lumen and a secondary cooling lumen;
providing an energy source capable of radiating a focused energy field having its highest energy levels distributed substantially along a line; and
inserting said energy source into one of said lumens, said energy source comprising a substantially arcuate ultrasound transducer having a radius of curvature larger than a radius of curvature of one of said lumens.

16. The thermotherapy method of claim 15 wherein said energy source comprises a plurality of ultrasound transducers.

17. The thermotherapy method of claim 16 wherein at least one of said ultrasound transducers is capable of being powered separately from the plurality of said ultraspund transducers.

18. The thermotherapy method as defined in claim 15 wherein said energy source comprises a radially segmented substantially cylindrical ultrasound transducer with each segment being capable of having individual power control.

19. The thermotherapy method as defined in claim 15 wherein said energy source comprises a longitudinally and radially segmented substantially cylindrical ultrasound transducer.

* * * * *